United States Patent [19]

Ober et al.

[11] Patent Number: 5,907,017
[45] Date of Patent: May 25, 1999

[54] SEMIFLUORINATED SIDE CHAIN-CONTAINING POLYMERS

[75] Inventors: Christopher K. Ober; Jianguo Wang; Edward J. Kramer, all of Ithaca, N.Y.

[73] Assignee: Cornell Research Foundation, Inc., Ithaca, N.Y.

[21] Appl. No.: 08/792,615

[22] Filed: Jan. 31, 1997

[51] Int. Cl.$^6$ .................... C08F 116/06; C08F 297/04; C08G 69/48
[52] U.S. Cl. ................ 525/332.3; 525/61; 525/420
[58] Field of Search .................... 525/332.3, 61, 525/420

[56] References Cited

U.S. PATENT DOCUMENTS

| | | | |
|---|---|---|---|
| 3,838,110 | 9/1974 | Villa | 526/248 |
| 3,839,743 | 10/1974 | Schwarcz | 117/124 R |
| 3,879,490 | 4/1975 | Villa | 525/122 |
| 3,880,949 | 4/1975 | Villa | 525/122 |
| 4,322,374 | 3/1982 | Martin et al. | 562/840 |
| 4,440,947 | 4/1984 | Arlt | 560/226 |
| 4,619,974 | 10/1986 | Mueller | 525/342 |
| 4,942,164 | 7/1990 | Baum et al. | 528/70 |
| 5,017,734 | 5/1991 | Baum et al. | 585/21 |
| 5,093,522 | 3/1992 | Bielefeldt et al. | 562/848 |
| 5,126,482 | 6/1992 | Nakai et al. | 554/150 |
| 5,166,313 | 11/1992 | Archibald et al. | 528/344 |
| 5,204,441 | 4/1993 | Baum et al. | 528/70 |

FOREIGN PATENT DOCUMENTS 57-180680  11/1982  Japan .

OTHER PUBLICATIONS

CAPLUS accession No. 1989:24348, Ishihara et al., Polymerization ability of perfluoroalkyoxy group–substituted sytrene derivatives and the surface characteristics, Kobunshi Ronbunshu, vol. 45, No. 8, pp. 653–659, 1988.

Wang et al., "Synthesis of Novel Low Surface Energy Semifluorinated alkyl Side Chain Ionenes," Polymer Preprints, vol. 37, No. 2, pp. 815–816, Aug. 1996.

Wang et al., "Self–assembly of fluorinated LC block copolymers with a stable low energy surface," Book of Abstracts, abstract No. 488, Apr. 1997.

Wang et al., "Liquid Crystalline, Semifluorinated Side Group Block Copolymers with Stable Low Energy Surfaces: Synthesis, Liquid Crystalline Structure, and Critical Surface Tension," Macromolecules, vol. 30, No. 7, pp. 1906–1914, Apr. 1997.

Ober et al., "Order within Order: Studies of Semifluorinated Block Copolymers," Macromolecular Symposia, vol. 118, pp. 701–706, Jun. 1997.

Ober, C. K., abstract titled, "Formation of Low Surface Energy Materials Using Polymers with Semifluorinated Groups," distributed at invited talk at 3M in St. Paul, MN on Mar. 19, 1996.

Ober, C. K., et al, abstract titled "Formation of Ordered Structures Via The Interplay of Liquid Crystallinity and Phase Separation in Block Copolymers," distributed incident to invited talk at Macro IUPAC '96, Seoul, Korea, Aug. 8, 1996.

Ober, C. K., abstract entitled "Simultaneous Organization on Different Molecular Legth Scales," distributed incident to Philadelphia, PA, Oct. 17, 1996 –Oct. 20, 1996.

Ober, C. K., et al, abstract titled "Simultaneous Organization on Different Length Scales: Liquid Crystallinity and Block Copolymers," distributed incident to invited talk at NATO Workshop on Manipulation of Order in Polymers, Il Ciccio, Italy, Jun. 1, 1996.

Ober, C. K., abstract titled "Self–organizing Semifluorinated Block Copolymers for the Formation of Hydrophobic Structures," distributed incident to invited talk at Kodak, Rochester, NY, Aug. 13, 1996.

Ober, C. K., abstract entitled "Simultaneous Organization on Different Molecular Length Scales," distributed incident to invited talk at Wright–Patterson AFB, Dayton, OH, Nov. 1, 1996.

*Primary Examiner*—Robert E. Sellers

[57] ABSTRACT

Fluorinated polymers for use per se or in a blend with compatible homopolymer or copolymer which is not fluorinated, for providing a low surface energy (anti-stick, non-wetting, low friction) surface which is stable on immersion in water, has a weight average molecular weight ranging from $10^3$ to $10^6$ and comprises backbone containing (a) methylene groups and (b) side chain bearing groups with side chain on each side chain bearing group having the formula —Q—$(CF_2)_q$F wherein Q comprises alkylene moiety and wherein the fluoroalkyl group attached to Q is spaced by r atoms from the atom in the backbone to which Q is attached, wherein q ranges from 6 to 15, r ranges from 6 to 18, and the ratio of q to r ranges from 0.6:1 to 1.8:1. Preferred fluorinated polymers include semifluorinated block copolymers of modified isoprene and styrene and semifluorinated ionenes.

13 Claims, 2 Drawing Sheets

SEMIFLUORINATED SIDE CHAIN-CONTAINING POLYMERS

This invention was made at least in part with Government support under Office of Naval Research Grant No. N00014-92-J-1246 and from the National Science Foundation.

TECHNICAL FIELD

This invention is directed to polymers containing fluorinated side chains.

BACKGROUND OF THE INVENTION

Fluorinated polymers are known and are used for providing low surface energy surfaces. Such surfaces have anti-stick, non-wetting and low friction properties.

Fluorinated ester side chain acrylic and methacrylic polymers are low surface energy coating materials which are commercially available.

Low surface energy fluorinated poly (amide urethane) block copolymers and other low surface energy polymers have been reported in the literature. See: Chapman, T. M., et al., Macromolecules, 28, 331–335 (1995); Chapman, T. M., et al., Macromolecules, 28, 2081–2085 (1995); Wynne, K. J., et al., Polym. Prepr. (Am. Chem. Soc., Div. Polym. Chem.), 36(1), 67–68 (1995); and Pike, J. K., et al., Chem. Mater., 8, 856–860 (1996).

However, the known polymers with fluorinated side chains do not have stable low surface energy properties when immersed in water, and over time in water the low surface energy properties are reduced due to movement of polar groups to the surface to change the polarity thereof. This changing of surface polarity over time, when due to contact with water, has been termed "surface reconstruction."

SUMMARY OF THE INVENTION

It has been discovered herein that by employing in a fluorinated polymer, side chains with perfluoroalkyl moiety containing a particular number of fluoroalkyl groups spaced from polymer backbone by a particular number of atoms in moiety containing alkylene group where a certain ratio of fluoroalkyl groups to spacing atoms is employed, a fluorinated polymer is provided which has stable low surface energy properties on immersion in water.

The term "stable" is used herein in relation to low surface energy properties, to mean providing an advancing water contact angle after immersion of a film of the fluorinated polymer in water for 48 hours which is no more than 15 degrees less than the advancing water contact angle in a dry film of the fluorinated polymer, i.e., in a film of the fluorinated polymer which has not been immersed in water. This stability means substantially no surface reconstruction occurs.

The contact angles herein are those determined using an NRC Contact Angle Goniometer Model 100-00 (Ramé-Hart Inc) at 20° C. on 1 micron thick films of fluorinated polymer on a silica or glass substrate. Advancing water contact angles are measured by injecting a 4 µl drop of water onto the film and measuring the advancing contact angle. The measurement on the dry film is carried out as described above before any immersion in water. The measurement after 48 hours of immersion in water is carried out by removing the film of polymer and substrate carrier from immersion in water, removing visually observable water with a towel and then measuring advancing contact angle.

The fluorinated polymers of the invention herein which are based on the above-described discovery have a weight average molecular weight ranging from about $1 \times 10^3$ to about $1 \times 10^6$ and comprise backbone containing (a) methylene groups and (b) side chain bearing groups with side chain on each side chain bearing group having the formula —Q—$(CF_2)_q$F wherein Q comprises alkylene moiety and the fluoroalkyl group attached to Q is spaced by r atoms from atom in the backbone to which Q is attached, wherein q ranges from 6 to 15, r ranges from 6 to 18, and the ratio of q to r ranges from 0.6:1 to 1.8:1.

In one preferred subgenus, each group (b) and side chain thereon is selected from the group consisting

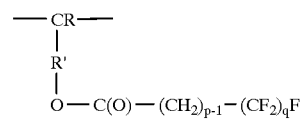

wherein R is selected from the group consisting of hydrogen and alkyl containing 1 to 6 carbon atoms and R' is alkylene or isoalkylene containing 1 to 10 carbon atoms and p is r minus 1 minus the number of chain atoms in R' and the number of chain atoms in R' ranges from 1 to 10 and q ranges from 6 to 15, r ranges from 6 to 18 and the ratio of q to r ranges from 0.6:1 to 1.8:1. In this subgenus, Q is R'—O—C(O)—$(CH_2)_{p-1}$ wherein R' and p are as defined in the preceding sentence.

In another preferred subgenus, each group (b) and side chain thereon is selected from the group consisting of

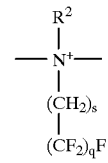

wherein $R^2$ is selected from the group consisting of hydrogen and alkyl containing 1 to 6 carbon atoms, s ranges from 6 to 18 and q ranges from 6 to 15. In this subgenus, Q is $(CH_2)_s$ and r is equal to s and the ratio of q to r ranges from 0.6:1 to 1.8:1.

Thus, the fluorinated polymers herein include polymers with no moieties bearing charges and polymers with moieties bearing charges.

Another embodiment herein is directed to compounds having the formula

wherein q ranges from 6 to 15, p ranges from 3 to 15 and X' is a halogen. These compounds are useful as reactants in a method of producing fluorinated polymers of the first subgenus mentioned above.

Still another embodiment herein is directed to compounds having the formula

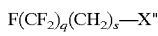

wherein s ranges from 6 to 18, q ranges from 6 to 15 and X' is a halogen. These compounds are useful as reactants in a method of producing fluorinated polymers of the second subgenus mentioned above.

DETAILED DESCRIPTION

Figure 1:
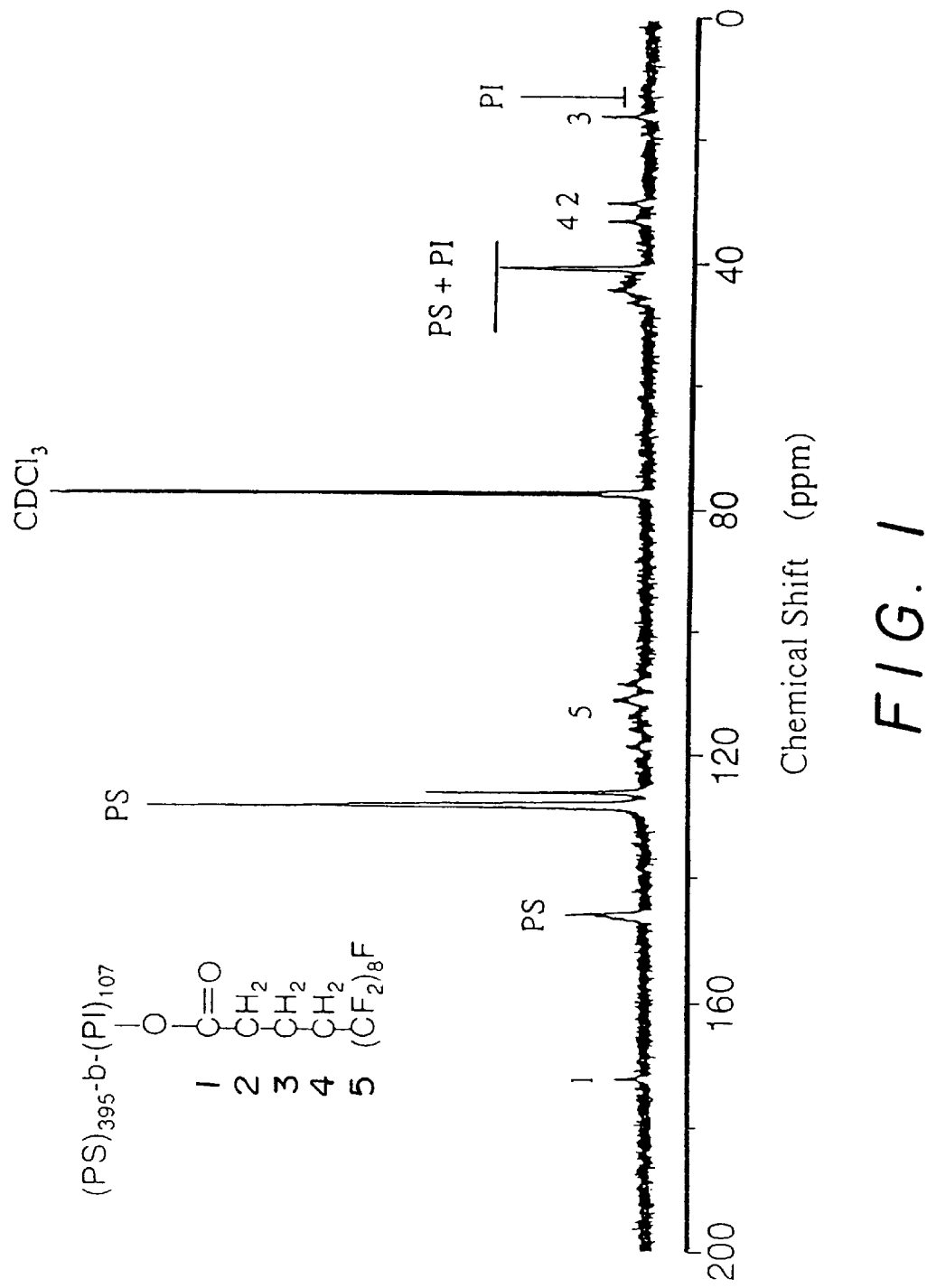
FIG. 1 depicts a $^{13}C$ NMR spectrum for the product of Example I.

The fluorinated polymers herein can be derived from any starting polymer which can be modified to contain side chain containing alkylene containing moiety followed by perfluoroalkyl moiety to provide q and r and the ratio of q to r as defined for the fluorinated polymers herein.

Starting material polymers include, for example, poly (styrene-b-1,2/3,4-isoprene) where b stands for block of poly 1,2/3,4-isoprene, i.e., block copolymers of styrene and 1,2/3,4-isoprene or of 1,2-isoprene and 3,4-isoprene having the formula

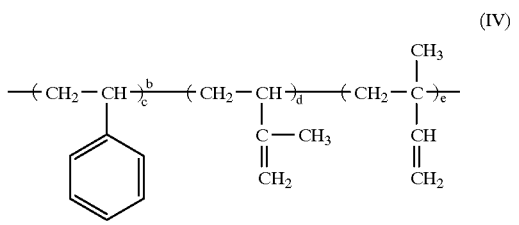

(IV)

where c ranges from 0 to 0.99, d ranges from 0.6 to 0.006 and e ranges from 0.4 to 0.004, where c+d+e equals 1.0 or having the formula

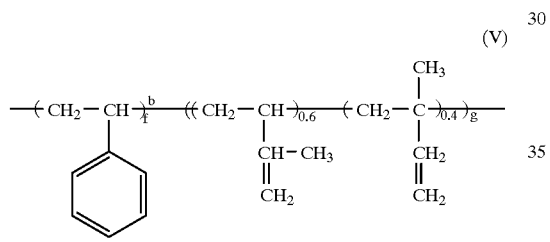

(V)

where f ranges from 0 to 0.99 and g ranges from 1.0 to 0.01 where f+g equals 1.0.

Starting material polymers also include, for example, polyamines having the structural formula

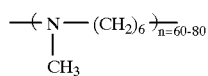

Starting material polymers also include, for example, polyvinyl alcohols.

The fluorinated polymers herein are prepared by reacting functionalized omega-perfluoroalkyl alkanes, e.g., omega-perfluoroalkyl-1-bromoalkanes, or omega-perfluoroalkyl acyl chlorides or omega-perfluoroalkyl acids with the starting material polymers.

We turn now to the subgenus where each group (b) and side chain thereon is selected from the group consisting of

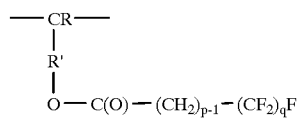

wherein R is selected from the group consisting of hydrogen and alkyl containing 1 to 6 carbon atoms and R' is alkylene or isoalkylene containing 1 to 10 carbon atoms and p is r plus 1 minus the number of chain atoms in R' and the number of chain atoms in R' ranges from 1 to 10 and q ranges from 6 to 15, r ranges from 6 to 18 and the ratio of q to r ranges from 0.6:1 to 1.8:1.

One species of this subgenus has the formula

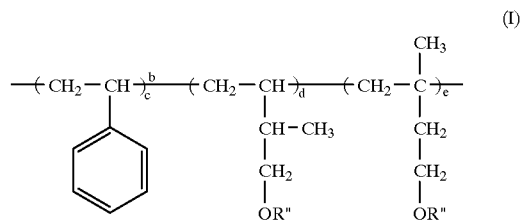

(I)

wherein c ranges from 0 to 0.99, d ranges from 0.6 to 0.006 and e ranges from 0.4 to 0.004, where c+d+e equals 1.0, and

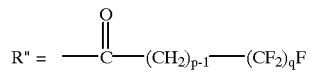

where q ranges from 6 to 15 and p ranges from 3 to 15 and the ratio of q to r which is p+3 ranges from 0.6:1 to 1.8:1 or the formula

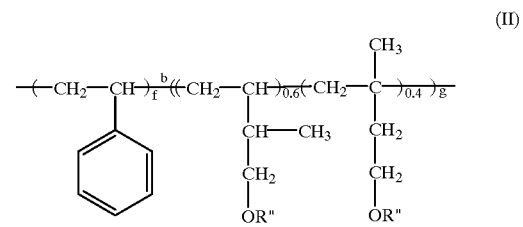

(II)

wherein f ranges from 0 to 0.99 and g ranges from 1.0 to 0.01, where f+g equals 1.0, and

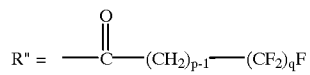

where q ranges from 6 to 15 and p ranges from 3 to 15 and the ratio of q to r which is p+3 ranges from 0.6:1 to 1.8:1.

Fluorinated polymers herein having the formula (I) include, for example, those where c is 0.786, d is 0.127 and e is 0.085, and the weight average molecular weight is about $1 \times 10^5$ and where q is 8 and p is 4 and the ratio of q to r is 1.1:1, where q is 8 and p is 6 and the ratio of q to r is 0.9:1, where q is 8 and p is 10 and the ratio of q to r is 0.6:1 and where q is 10 and p is 10 and the ratio of q to r is 0.8:1.

Fluorinated polymers herein having the formula (II) include, for example, those where q is 8 and p is 4 and the ratio of q to r is 1.1:1 and where f is 0 and g is 1.0 and the weight average molecular weight is $10^5$–$10^6$, where f is 0.23 and g is 0.77 and weight average molecular weight is $10^4$–$10^6$, where f is 0.42 and g is 0.58 and the weight average molecular weight is about $10^5$, where f is 0.81 and g is 0.19 and the weight average molecular weight is about $10^5$ and where f is 0.93 and g is 0.07 and the weight average molecular weight is about $10^5$.

Terminating groups for the backbone of the fluorinated polymers of the formulas (I) and (II) include, for example, hydrogen and alkyl containing 1 to 6 carbon atoms.

We turn now to a method of making the fluorinated polymers of the formulas (I) and (II).

The starting material polymers (IV) and (V) can be obtained in an anionic polymerization as described in Mao, G. P., et al., Polymer Prep. 34(2), 710 (1993), which is incorporated herein by reference. This reaction is carried out using alkyl lithium at −78° C.

The starting material polymers (IV) and (V) are reacted to convert the double bonds in the isoprene side chains to alcohol groups, for example, in a hydroboration reaction as described in Mao, G. P., et al., Polymer Prep. 34(2), 710 (1993) except that the reaction should be kept free from moisture and oxygen and workup of the hydroxylated block copolymer is preferably carried out by precipitating the product into a 0.5–1.0M KOH water/methanol solution to remove sodium boronic acid and dihydroxycyclooctane, filtering the solid product, then dissolving the product in methanol/tetrahydrofuran solution and reprecipitating it three times, then drying the product for 8 to 16 hours in a vacuum oven at 60° C. The precipitation in a basic solution prevents hydrolysis of $NaB(OH)_4$ to boronic acid $B(OH)_3$ which will crosslink the hydroxylated block copolymer.

The hydroxylated block copolymer is reacted with semifluorinated acid halide to provide the fluorinated polymer.

The semifluorinated acid halide has the formula $$F(CF_2)_q-(CH_2)_{p-1}COX'$$

wherein q ranges from 6 to 15, p ranges from 3 to 15 and X' is a halogen. X' is preferably Cl⁻ but may also advantageously be Br⁻ or I⁻.

The semifluorinated acid halide is preferably prepared in a three step process which is described below.

In the first step, semifluorinated alcohols $F(CF_2)_q-(CH_2)_p-OH$ are prepared by free radical addition of perfluoroalkyliodide to omega-alkene-1-ol as described in H öpken, J., New Polymeric Mater., 2, 339 (1991), which is incorporated herein by reference. This reaction step is described in more detail later.

In the second step, the semifluorinated alcohols are oxidized to the semifluorinated acids $F(CF_2)_q-(CH_2)_{p-1}-COOH$, very preferably using nitrogen dioxide as an oxidizing agent. The nitrogen dioxide is preferably added at low temperature, e.g., −40° C., then allowed to warm to room temperature and then reacted, very preferably at 55° C. for 48 hours. Pure product can be recovered by sublimation at 0.5 mm Hg.

In the third step, the acid halide is prepared preferably by reacting the acid with thionyl halide, e.g., thionyl chloride, preferably at room temperature for 30 minutes and then at 40° C. for 2 hours.

The reaction of the hydroxylated block copolymer and an excess of semifluorinated acid halide is preferably carried out in anhydrous tetrahydrofuran and pyridine, very preferably at 45° C. for 10 hours after tetrahydrofuran solution of semifluorinated acid halide is slowly injected into a solution of the hydroxylated block copolymer in anhydrous tetrahydrofuran and pyridine. After the reaction is completed, the excess acid chloride is converted to ester by reaction with methanol, and ester and pyridine salt are removed by pouring the reaction mixture into methanol/water solution. The fluorinated polymer can be purified by dissolving in tetrahydrofuran, washing with water/methanol and drying in a vacuum oven.

We turn now to the compounds herein where polyvinyl alcohol is the starting material. The starting material is reacted with semifluorinated acid halide as described above to provide fluorinated polymers herein.

We turn now to the subgenus where each group (b) and the side chain thereon is selected from the group consisting of

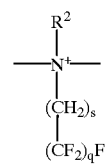

wherein $R^2$ is selected from the group consisting of hydrogen and alkyl containing 1 to 6 carbon atoms, s ranges from 6 to 18 and q ranges from 6 to 15. Compounds of this subgenus may be referred to as semifluorinated alkyl side chain ionenes, i.e., having semifluorinated alkyl side chains directly connected to nitrogen in a quaternary ammonium backbone by a covalent bond.

A species of this subgenus has the formula

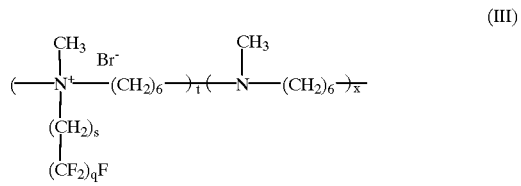

(III)

wherein t ranges from 0.6 to 1.0, x ranges from 0.4 to 0, s ranges from 6 to 18, q ranges from 6 to 15 and the ratio of q to r (which is s in this case) ranges from 0.6:1 to 1.8:1. These have a degree of quaternization ranging from 60 to 100%.

Fluorinated polymers of the invention herein having the formula (III) include, for example, those where t is 0.85 and x is 0.15 and where s is 6 and q is 8 and the ratio of q to r is 1.3:1, where s is 10 and q is 8 and the ratio of q to r is 0.8:1, where s is 10 and q is 10 and the ratio of q to r is 1:1, and where s is 10 and q is 12 and the ratio of q to r is 1.2:1.

Terminating groups for the backbones fluorinated polymers include, for example, hydrogen and alkyl containing 1 to 6 carbon atoms.

We turn now to a method of making the fluorinated polymers of the invention herein having the formula (III).

The starting material polymers for preparing these fluorinated polymers are polyamines having the formula

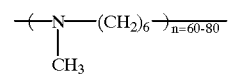

The polyamines can be prepared from commercially available materials as follows:

Crude nylon salt is prepared by adding adipic acid to a stirring mixture of an equimolar amount of N,N'-dimethyl-1,6-hexanediamine in absolute ethanol at 60° C. and then maintaining the reaction mixture at 70–80° C. for 1 hour. Crude nylon salt can be obtained by evaporating the ethanol and purification can be carried out by recrystallizing from ethanol and drying under vacuum.

The nylon salt is converted to polyamide of the formula

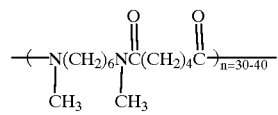

In a first step, the nylon salt is heated gradually in a sealed tube to 300° C. is then maintained at this temperature for 24 to 36 hours to obtain oligomerization. Then the sealed tube is opened and purged with nitrogen to remove water for 2 hours at above 200° C. followed by removing more water by maintaining at above 200° C. for 18 hours under vacuum.

The polyamide is converted to the polyamine starting material polymer in a homogeneous reduction reaction. Use of borane/dimethylsulfide in tetrahydrofuran at 50–55° C. produces quantitative reaction without detectable degradation. The tetrahydrofuran and dimethylsulfide are distilled off and degassed HCl is added to destroy excess borane. Recovery of the polyamine is obtained by dumping the reaction mixture into 20% NaOH and washing the gel like product until the pH is close to neutral, dissolving in diethyl ether, drying with $Na_2CO_3$ and then in a vacuum oven.

The polyamine is reacted with a semifluorinated haloalkane to provide the fluorinated polymer.

The semifluorinated haloalkane has the formula

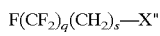

wherein s ranges from 6 to 18, q ranges from 6 to 15 and X" is halogen or $SO_3H^-$. X" is preferably bromo but may also advantageously be $Cl^-$, $I^-$, or $SO_3H^-$.

The semifluorinated haloalkane is preferably prepared by forming the corresponding omega-perfluoroalkyl alkanol and converting the alkanol to the haloalkane.

The omega-perfluoroalkylalkanols can be prepared by free radical addition of perfluoroalkyl iodide and omega-alkene-1-ol in a procedure similar to that reported by Höpken, J., et al., New Polymeric Mater. 2, 339 (1991) which is incorporated herein by reference, and dehalogenation. An excess of omega-alkene-1-ol is utilized and remaining omega-alkene-1-ol is preferably distilled from the free radical addition product to eliminate possible side reactions during dehalogenation. Dehalogenation is preferably carried out by reduction with tributyltin hydride in toluene. Workup preferably comprises decomposing remaining tributyltin hydride by pouring into methanol, evaporating the methanol, recrystallizing the products from toluene and then causing sublimation under vacuum at a temperature below the melting point.

The alkanol is converted to the haloalkane, preferably by reacting with 50–100% excess carbon tetrahalide, preferably tetrabromide, and triphenylphosphine, at −5 to +10° C. for 6 to 8 hours where the temperature is such as to prevent the alkanol from precipitating out. Product can be purified by using a short silica column with diethyl ether as elution solvent to separate product from triphenylphosphine by-product (the column absorbs the triphenylphosphine oxide) and then recovering high purity product by distillation or sublimation.

The reaction of the polyamine with semifluorinated haloalkane is carried out using high concentrations of reactants, an aprotic polar solvent, e.g., ethanol/N,N'-dimethyl formamide, and high reaction temperature, e.g., 65 to 70° C., and a long reaction time, e.g., two to four weeks, to obtain 80 to 90% quaternization.

We turn now to the properties of the fluorinated polymers herein.

They all have an advancing water contact angle for the dry film (i.e., has not been immersed in water) of greater than 100 degrees.

They all have an advancing water contact angle after immersion in water of a film of the fluorinated polymer for 48 hours which is no more than 15 degrees less than the advancing contact angle in a dry film of the fluorinated polymer.

They all have critical surface tensions of 8–10 dynes/cm or less as measured by a Zissman plot.

In the measurement of the contact angles, films of fluorinated polymers of formulas (I) and (II) are prepared by slowly evaporating a 2% fluorinated polymer/$\alpha,\alpha,\alpha$-trifluorotoluene solution on a silica wafer at room temperature. In the measurement of contact angles, films of fluorinated polymers of the formula (III) are prepared by spin-coating a 5% polymer solution in methanol on a glass cover at room temperature.

The fluorinated polymers of the formulas (I) and (II) have weight average molecular weights ranging from $1 \times 10^3$ to $1 \times 10^5$ and a dispersity, Mw/Mn, ranging from 1.03 to 1.15.

For the fluorinated polymers of the formulas (I) and (II), the advancing water contact angle in a dry film is 8 to 15 degrees higher than the receding contact angle in a dry film. This difference means that hysteresis in the films is much smaller than usually reported for many low energy surfaces. The receding water contact angles are measured by removing 3 $\mu$l from the 4 $\mu$l droplet of water injected for measuring the advancing water contact angle.

The fluorinated polymers of the formula (III) have weight average molecular weights ranging from $10^3$ to $10^6$. They are wax-like white solids at room temperature. They are soluble in methanol and dimethylformamide but insoluble in non-polar solvents.

The fluorinated polymers herein are useful for peel off backings for self-stick labels, non-stick surfaces to prevent accumulation of biological debris, non-toxic anti-fouling release coatings for ship hulls (to prevent attachment, for example, of barnacles), anti-graffiti surfaces, self-lubricating surfaces, and stain-resistant fabrics.

The fluorinated polymers herein can be used in blends with compatible non-fluorinated polymers where the fluorinated polymer constitutes from 0.1 to 10% by weight of the blend. For example, the fluorinated polymers herein, of the formulas (I) and (II), may be blended with polystyrene, polyethylene, or other polymers; and the fluorinated polymers of the formula (III) may be blended with thermoplastics, elastomers, or thermosets. Heating of solidified blend at a temperature above the glass transition temperature of the matrix polymer will cause the fluorinated polymers to migrate to the surface even though as little as 1% by weight fluorinated polymer is present.

The invention is illustrated in the following examples. Each contact angle value given in the examples and comparative examples is an average of four measurements. In Examples I–IV and Comparative Example I, the synthesized polymers each contained 395 styrene groups, 64 1,2-isoprene groups, and 43 3,4-isoprene groups.

EXAMPLE I

Synthesis of Fluorinated Polymer of the Formula (I) Where c is 0.786, d is 0.127, e is 0.085, q is 8 and p is 4 and the Ratio of q to r is 1.1 to 1

The poly(styrene-b-1,2 and 3,4-isoprene) starting polymer was prepared as described in Mao, G. P., et al., Polymer Prep. 34(2), 710 (1993).

Hydroboration to provide hydroxylated block copolymer was carried out as described in Mao, G. P., et al., Polymer Prep. 34(2), 710 (1973) with the reaction being kept free from moisture and oxygen except that workup was carried out as follows. The product was carefully precipitated into a 0.5–1.0M KOH water/methanol solution, solid product was filtered and dissolved in a methanol/tetrahydrofuran solution and reprecipitated three times and the product was dried overnight in a vacuum oven at 60° C.

Semifluorinated acid fluoride reactant was made as follows. The semifluorinated alcohol $F(CF_2)_8(CH_2)_4OH$ was synthesized by radical addition of perfluorooctyl iodide to omega-butene-1-ol by the procedure described in Höpken, J., New Polymeric Mater., 2, 339 (1991). Then 3.95 g (8.0 mmol) $F(CF_2)_8(CH_2)_4OH$ was placed in a glass tube reactor (20×200 mm) equipped with a small magnetic stir bar, and sealed with a Teflon stopcock. At –40° C., 1.9 g (40 mmol) $NO_2$ was introduced into the reactor and was warmed to room temperature (18° C.) over a period of 50 hours. The stopcock was closed after the blue solid gradually turned to brown, and the reaction was allowed to run at room temperature for 1 hour, while the solid white alcohol reacted and dissolved in the dark brown $NO_2$. The reactor was then heated to 55° C. over a period of 1 hour and held at this temperature for 48 hours. The reaction was then allowed to cool to room temperature; then the stopcock was opened while excess nitrogen dioxide was removed by a vacuum aspirator. The white product was purified by sublimation just below its melting point to yield 3.26 g $F(CF_2)_8(CH_2)_3COOH$ (yield 78.7%). 1H NMR (CDC13, δ in ppm), 2.49 (t, 2H, J=7.0 Hz, —CH2COOH), 1.95 (p, 2H, J=7.2 Hz, —CH2CH2CH2—), 2.17 (ttd, 2H, —CF2CH2CH2—). Then, 1.50 g (3 mmol) solid $F(CF_2)_8(CH_2)_3COOH$ containing 0.5 ml $SO_2Cl_2$ was added dropwise to a 10 ml round bottomed flask. After proceeding at room temperature for 30 minutes, the reaction mixture was heated to 40° C. for 2 hours. Vacuum was used to eliminate excess $SO_2Cl_2$ to yield 1.32 g $F(CF_2)_8(CH_2)_3COCl$.

Reaction of hydroxyated block copolymer and $F(CF_2)_8(CH_2)_3COOH$ was carried out in a dry 5 ml flask, in which 300 mg of the hydroxylated block copolymer (0.642 mmol OH) was dissolved in 2 ml anhydrous tetrahydrofuran and 0.5 ml pyridine. Then 420 mg (0.80 mmol) $F(CF_2)_8(CH_2)_3COCl$ in tetrahydrofuran solution (10% acid chloride) was injected over a period of 5 minutes through a rubber septum. During the reaction, solid pyridine/hydrochloride salt precipitated out. The reaction was maintained at 45° C. for another 10 hours. Once the reaction was complete, 1 ml anhydrous methanol was injected into the flask to convert the excess acid chloride to ester. The polymer solution was poured into copious amounts of a 1:1 methanol/water solution to remove excess semifluorinated ester and pyridine salt. The polymer was collected, dissolved in tetrahydrofuran, and washed with water/methanol. This procedure was repeated five times, then the product was dried overnight at 60° C. in a vacuum oven. A $^{13}C$ NMR spectrum (obtained on a Variant FX-400 at 100.12 MHz using deuterated chloroform as a solvent with chemical shifts referenced to tetramethylsiloxane is depicted in FIG. 1 whereon PS stands for polystyrene and b-(PI) stands for a block of polyisoprene. X-ray diffraction (obtained using a SCINTAG Θ to Θ diffractometer and Ni-filtered cu X-ray tube, Kα=1.5418 angstroms, operated at 45 KV and 40 mA) gave D spacing in angstroms of 32.2 (strong), 16.2 (medium), 10.7 (weak), 5.06 (broad). The weight average molecular weight was determined to be about $1\times10^5$, and the dispersity, Mw/Mn, determined from gel permeation chromatography on four Waters Styragel HT columns operating at 36° with tetrahydrofuran as a solvent operating at 0.3 ml/min. was 1.07. The advancing water contact angle in a dry film was determined to be 120° and the receding water contact angle in a dry film was determined to be 109, and the critical surface tension for water was determined to be 8.5 dynes/cm.

EXAMPLE II

Synthesis of Fluorinated Polymer of the Formula
(I) Where c is 0.786, d is 0.127, e is 0.085, q is 8 and p is 6 and the Ratio of q to r is 0.9:1

The synthesis was carried out as in Example I with equimolar amounts of reactants being used except that the semifluorinated alcohol made was $F(CF_2)_8(CH_2)_6OH$ and the semifluorinated acid made was $F(CF_2)_8(CH_2)_5COOH$ and the acid was found to have 1H NMR (CDC13, δ in ppm), 2.37 (t, 2H, J=7.2 Hz, —CH2COOH), 1.67 (2H, —CH2CH2COOH), 1.49(2H, —CF2CH2CH2CH2), 1.63 (2H, —CF2CH2CH2), 2.05 (2H, —CF2CH2—). X-ray diffraction data obtained as in Example I gave D spacing in angstroms of 35.2 (strong), 17.6 (weak), 11.7 (medium) and 4.95 (broad). The weight average molecular weight was determined to be $1.2\times10^5$, and the dispersity, Mw/Mn, determined as in Example I, was 1.06. The advancing water contact angle in a dry film was determined to be 120 degrees and the receding water contact angle in a dry film was determined to be 108 degrees, and the critical surface tension for water was determined to be 8.5 dynes/cm.

EXAMPLE III

Synthesis of Fluorinated Polymer of the Formula
(I) Where c is 0.786, d is 0.127, e is 0.085, q is 8 and p is 10 and the Ratio of q to r is 0.6:1

Figure 2:
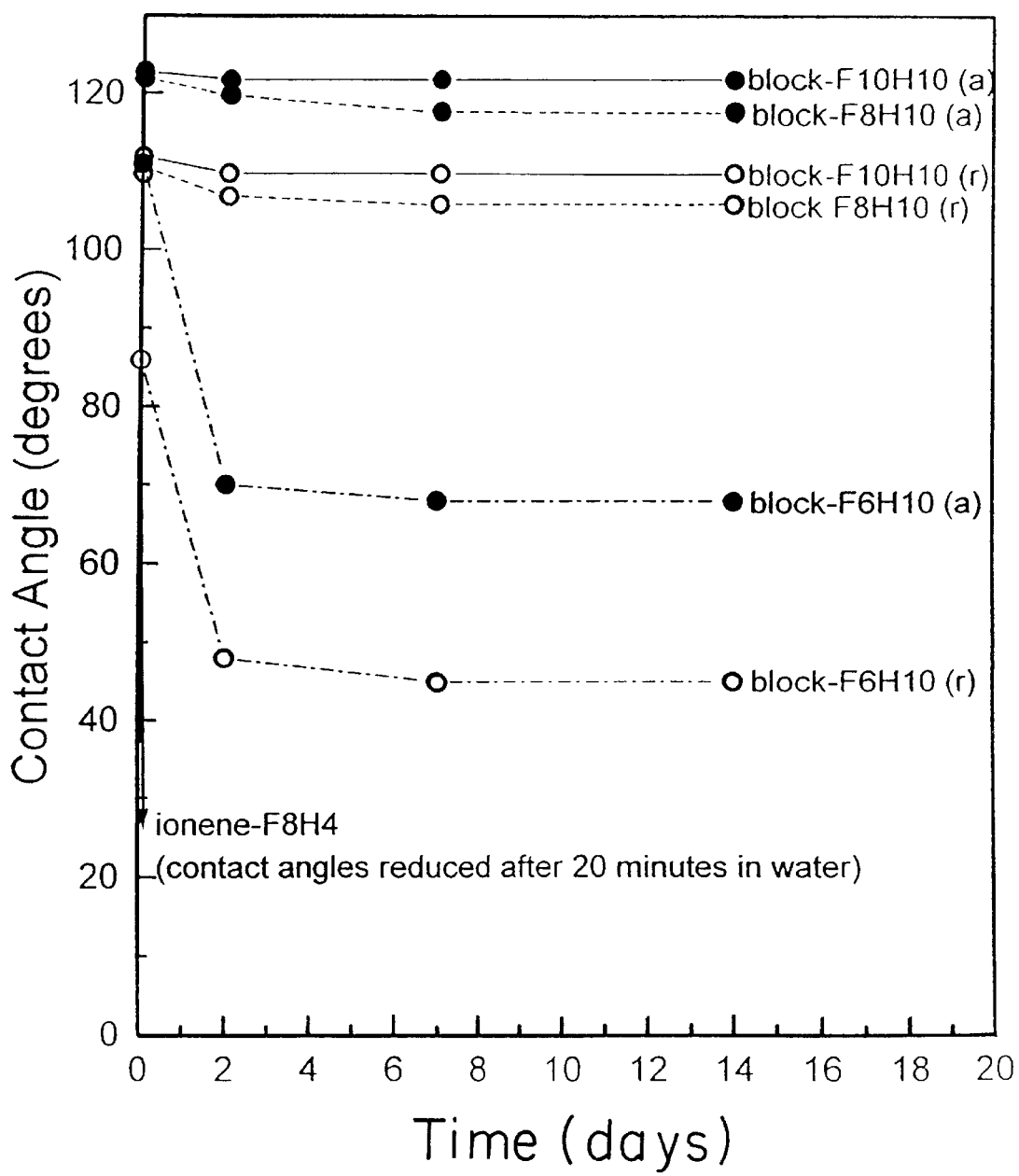
FIG. 2 contains water contact angle data for Examples III and IV and Comparative Examples I and II.

The synthesis was carried out as in Example I with equimolar amounts of reactants being used except that the semifluorinated alcohol made was $F(CF_2)_8(CH_2)_8OH$ and the semi luorinated acid made was $F(CF_2)_8(CH_2)_9COOH$ and the acid was found to have 1H NMR (CDC13, δ in ppm), 2.34(t, J=7.3 Hz, —CH2COOH), 1.62 (2H, —CH2CH2COOH), 1.28 and 1.29 (10H, (CH2)5 CH2CH2COOH), 1.58 (2H, —CF2CH2CH2—), 2.03 (2H, —CF2CH2). X-ray diffraction data on the fluorinated polymer obtained as in Example I gave D spacing in angstroms of 40.1 (strong), 13.4 (weak), 4.83 (broad). The weight average molecular weight for the fluorinated polymer was determined to be about $1\times10^5$, and the dispersity, Mw/Mn, determined as in Example I was 1.08. The critical surface tension for water was determined to be 8.2 dynes/cm. Data on contact angles is set forth in FIG. 2 wherein the fluorinated polymer of this example is denoted block-F10H8 and (a) means advancing water contact angle and (r) means receding water contact angle and time is the amount of time immersed in water. As indicated in FIG. 2, the advancing water contact angle in a dry film was determined to be 122 degrees and the advancing water contact angle after 48 hours (two days) immersion in water was determined to be about 120 degrees, so the difference between advancing water contact angle in a dry film and the advancing water contact angle after immersion in water for 48 hours was determined to be 2 degrees. As indicated in FIG. 2, the advancing water contact angle after two weeks (14 days) immersion in water was about the same as after 48 hours immersion in water. As indicated in FIG. 2, the receding water contact angle in a dry film was determined to be about 110 degrees and the difference between the advancing water contact angle and the receding water contact angle in a dry film was about 12 degrees.

EXAMPLE IV

Synthesis of Fluorinated Polymer of the Formula (I) Where c is 0.786, d is 0.127, e is 0.085, q is 10 and p is 10 and the Ratio of q to r is 0.8:1

The synthesis was carried out at in Example I with equimolar amounts of reactants being used except that the semifluorinated alcohol made was $F(CF_2)_{10}(CH_2)_{10}OH$ and the semifluorinated acid made was $F(CF_2)_{10}(CH_2)_9COOH$ and the acid was found to have the same 1H NMR results as for the semifluorinated acid of Example III. X-ray diffraction data obtained as in Example I gave D spacing in angstroms of 46.3 (very strong), 15.7 (strong), 4.85 (broad). The weight average molecular weight of the fluorinated polymer was estimated to be about $1 \times 10^5$. The critical surface tension for water for the fluorinated polymer was determined to be 8.0 dynes/cm. Data on contact angles is set forth in FIG. 2 wherein the fluorinated polymer of this example is denoted block-F10H10 and (a) means advancing water contact angle and (r) means receding water contact angle and time is the amount of time immersed in water. As indicated in FIG. 2 the advancing water contact angle in a dry film was determined to be 123 degrees and the advancing water contact angle after 48 hours (two days) immersion in water was determined to be about 121 degrees and the difference is 2 degrees. As indicated in FIG. 2, the advancing water contact angle after two weeks (14 days) immersion in water was about the same as after 48 hours immersion in water. As indicated in FIG. 2, the receding water contact angle in a dry film was determined to be about 112 degrees and the difference between the advancing water contact angle and the receding water contact angle in a dry film was about 11 degrees.

COMPARATIVE EXAMPLE I

Fluorinated Polymer of Formula (I) Where c is 0.786, d is 0.127, e is 0.085, q is 6 and p is 10 and the Ratio of q to r is 0.5:1

The synthesis was carried out as in Example I with equimolar amounts of reactants being used except that the semifluorinated alcohol made was $F(CF_2)_6(CH_2)_{10}OH$ and the semifluorinated acid made was $F(CF_2)_6(CH_2)_9COOH$ and the acid was found to have 1H NMR data as follows: 1H NMR (CDC13, δ in ppm), 2.34(t, J=7.3 Hz, —CH2COOH), 1.62 (2H, —CH2CH2COOH), 1.28 and 1.29 (10H, (CH2)5CH2CH2COOH), 1.58 (2H, —CF2CH2CH2—), 2.03 (2H, —CF2CH2). X-ray diffraction data obtained as in Example I for the fluorinated polymer gave D spacing in angstroms of 33.8 (strong), 17.0 (very weak) and 4.84 (very broad). The weight average molecular weight for the fluorinated polymer was estimated to be $1 \times 10^4 - 1 \times 10^6$ and the dispersity, Mw/Mn, determined as in Example I, was 1.05. The critical surface tension for water was determined to be 10.8 dynes/cm. Data on contact angle is set forth in FIG. 2 where the fluorinated polymer of this comparative example is denoted block-F6H10 and (a) means advancing water contact angle and (r) means receding water contact angle and time is the amount of time immersed in water. As indicated in FIG. 2, the advancing water contact angle in a dry film was determined to be 111 degrees and the advancing water contact angle after 48 hours (two days) was determined to be about 70 degrees and the difference is 41 degrees. As indicated FIG. 2, the receding water contact angle in a dry film was determined to be 86 degrees and the difference between the advancing water contact angle and the receding water contact angle in a dry film was about 25 degrees.

EXAMPLE V

Synthesis of Fluorinated Polymer of the Formula (II) Containing No Styrene Groups and 191 1,2/3, 4-Isoprene Groups (f=0 and g=1.0), q is 8 and p is 4 and Ratio of q to r is 1.1 to 1

The synthesis was carried out as in Example I except that the starting polymer was prepared by the procedure described in Mao, G. P., et al., Polymer Prep. 34(2), 710 (1993), to give final product with no styrene groups and 191 1,2/3,4-isoprene groups. X-ray diffraction data obtained on the fluorinated polymer as described in Example I gave D spacing in angstroms of 34.3 (very strong), 16.8 (strong), 11.42 (medium), 4.93 (sharp). The weight average molecular weight was estimated to be $10^5 - 10^6$. The advancing water contact angle in a dry film was determined to be 121 degrees and the receding water contact angle in a dry film was determined to be 111 degrees, and the critical surface tension of the fluorinated polymer for water was determined to be 8.1 dynes/cm.

EXAMPLE VI

Synthesis of Fluorinated Polymer of the Formula (II) With 48 Styrene Groups and 162 1,2/3,4-Isoprene Groups (f=0.23 and g=0.77), q is 8 and p is 4 and the Ratio q to r is 1.1 to 1

The synthesis was carried out as in Example I except that the starting polymer was prepared by the procedure described in Mao, G. P., et al., Polymer Prep. 34(2), 710 (1993), to give final product with 48 styrene groups and 162 1,2/3,4-isoprene groups. X-ray diffraction data obtained on the fluorinated polymer as described in Example I gave D spacing in angstroms of 33.7 (strong), 16.7 (medium), 11.23 (weak), 4.979 (sharp). The weight average molecular weight was estimated to be $10^4 - 10^6$. The advancing water contact angle in a dry film was determined to be 120 degrees and the receding water contact angle in a dry film was determined to be 109 degrees, and the critical surface tension of the fluorinated polymer in water was determined to be 8.3 dynes/cm.

EXAMPLE VII

Synthesis of Fluorinated Polymer of the Formula (II) With 138 Styrene Groups and 187 1,2/3,4-Isoprene Groups (f=0.42 and g=0.58), q is 8 and p is 4 and the Ratio q to r is 1.1 to 1

The synthesis was carried out as in Example I except that the starting polymer was prepared by the procedure described in Mao, G. P., et al., Polymer Prep. 34(2), 710 (1993), to give final product with 138 styrene groups and 187 1,2/3,4-styrene groups. X-ray diffraction data obtained on the fluorinated polymer as described in Example I gave D spacing in angstroms of 33.9 (strong), 16.7 (weak), 11.11 (weak), 4.98 (broad). The weight average molecular weight was estimated to be $10^5$. The advancing water contact angle in a dry film was determined to be 120 degrees and the receding water contact angle in a dry film was determined to be 109 degrees, and the critical surface tension of the fluorinated polymer in water was determined to be 8.5 dynes/cm.

EXAMPLE VIII

Synthesis of Fluorinated Polymer of the Formula (II) Containing 635 Styrene Groups and 150 1,2/3, 4-Isoprene Groups (f=0.81 and g=0.19), q is 8 and p is 4 and the Ratio q to r is 1.1 to 1

The synthesis was carried out as in Example I except that the starting polymer was prepared by the procedure described in Mao, G. P., et al., Polymer Prep. 34(2), 710 (1993), to give final product with 635 styrene groups and 150 1,2/3,4-isoprene groups. X-ray diffraction data obtained on the fluorinated polymer as described in Example I gave D spacing in angstroms of 32.3 (strong), 16.0 (weak), 10.74 (weak), 5.01 (broad). The weight average molecular weight was determined to be $10^5$, and the dispersity, Mw/Mn, determined as in Example I, was 1.07. The advancing water contact angle in a dry film was determined to be 118 degrees and the receding water contact angle in a dry film was determined to be 107 degrees, and the critical surface tension of the fluorinated polymer for water was determined to be 8.5 dynes/cm.

EXAMPLE IX

Synthesis of Fluorinated Polymer of the Formula (II) Containing 1692 Styrene Groups and 137 1,2/3, 4-Isoprene Groups (f=0.93 and g=0.07), q is 8 and p is 4 and the Ratio q to r is 1.1 to 1

The synthesis was carried out as in Example I except that the starting polymer was prepared by the procedure described in Mao, G. P., et al., Polymer Prep. 34(2), 710 (1993), to give final product with 1692 styrene groups and 137 1,2/3,4-isoprene groups. X-ray diffraction data obtained on the fluorinated polymer as described in Example I gave D spacing in angstroms of about 36 (weak). The weight average molecular weight was determined to be $10^5$, and the dispersity, Mw/Mn, determined as in Example I, was 1.10. The advancing water contact angle in a dry film was determined to be 108 degrees and the receding water contact angle in a dry film was determined to be 95 degrees, and the critical surface tension of the fluorinated polymer for water was determined to be 9.9 dynes/cm.

EXAMPLE X

Synthesis of Fluorinated Polymer of the Formula (III) Where t is 0.86, x is 0.14, q is 8 and s is 6 and the Ratio q to r is 1.3 to 1

Portions of 0.1 mol adipic acid were slowly added to a stirring mixture of 40 ml absolute ethanol and 0.1 mol N,N'-dimethyl-1,6-hexanediamine at 60° C., and then the reaction was raised to 80° C. for 1 hour. Crude nylon salt was obtained by rotoevaporation of the ethanol and layer-like crystal nylon salt was prepared by recrystallizing in a small amount of ethanol (10 ml) twice followed by drying in a vacuum oven at room temperature.

Then 8 g nylon salt was added to a long pyrex glass tube, and the air was exchanged with nitrogen before sealing the tube. The sealed glass tube was buried in a sand bath and heated gradually to 300° C. over 4 hours, and the reaction was kept at this temperature for another 24 hours. Then the top of the glass tube was opened and purged with nitrogen to remove water at 250° C. for 2 hours. Then, at 250° C., the tube was connected to a vacuum line at $3.5 \times 10^{-3}$ mm Hg for 18 hours. The product was polyamide of about 35 repeating units and had a slightly brown color. Analysis of the product gave $^1$H NMR (CDCl$_3$, δ in ppm), 2.87, 2.94 (3H, NCH$_3$), 2.31 (2H, COCH$_2$), 1.45 (4H,COCH$_2$CH$_2$), 3.31 (4H, NCH$_3$CH$_2$), 1.65 (4H, NCH$_3$CH$_2$CH$_2$), 1.28 (2H, NCH3CH$_2$CH$_2$CH$_2$).

The polyamide was converted to poly(N,N'-dimethyl-1, 6-hexanediamine) as follows: In a dry flask equipped with a condenser topped with a nitrogen inlet and bubbler connected by a rubber septum from the top of the condenser, 5 g (39.4 mmol) polyamide was dissolved in 100 ml anhydrous tetrahydrofuran under nitrogen. The solution was heated in an oil bath at 50° C. before 90 ml of a 2M borane/dimethylsulfide solution was directly transferred by a double ended needle. During the reaction, a polyamine/borane complex formed and the brown solution changed in color to light yellow. After 24 hours, the tetrahydrofuran and dimethylsulfide were distilled off. Then 50 ml of degassed 6N HCl was carefully added at 60° C. to in order to destroy any excess borane. The decomposition reaction was continued until no gas was given off. The product, polyamine was recovered by dumping the reaction mixture into 300 ml of 20% NaOH solution and the gel like product was washed with water until the pH was about 8–9. The product was dissolved in diethyl ether and dried with Na$_2$CO$_3$ and then was dried in a vacuum oven at 40° C. for two days. Analysis of the product gave $^1$H NMR (CDCl$_3$, δ in ppm), 2.16, (3H, NCH$_3$), 2.27 (4H, NCH$_3$CH$_2$), 1.49 (4H, CH$_3$NCH$_2$CH$_2$), 1.26 (4H, CH$_3$NCH$_2$CH$_2$CH$_2$); $^{13}$C NMR (CDCl$_3$, δ in ppm), 57.75 (CH$_3$NCH$_2$), 42.14 (CH$_3$NCH$_2$), 27.50 (CH$_3$NCH$_2$CH$_2$CH$_2$), 27.15 (CH$_3$NCH$_2$CH$_2$CH$_2$).

The polyamide was reacted with the semifluorinated omega-perfluoroalkyl 1-bromoalkane F(CF$_2$)$_8$(CH$_2$)$_6$Br.

The F(CF$_2$)$_8$(CH$_2$)$_6$Br was prepared as follows: In a 100 ml three-necked flask equipped with a condenser, bubbler, nitrogen inlet and magnetic stirrer, 30 mmol (16.38 g) of perfluorooctyl iodide and 45 mmol omega-hexene-1-ol (99%) were placed in an oil bath and heated to 80° C. Then 82 mg (0.5 mmol) azoisobutyronitrile (AIBN) was added in small portions over 45 minutes, and then reaction was carried out with stirring for 5 hours. The raw wax-like semifluorinated alkane iodide, in a small flask, was placed under vacuum to evacuate the excess omega-alkene-1-ol and low boiling substances. Direct dehalogenation was attained by adding 10 ml toluene, 0.493 g (3 mmol) AIBN and 17.44 g of tri-n-butyl tin hydride at 80° C. for 18 hours. Then the solution was poured into 200 ml methanol to decompose the tributyl tin. Rotoevaporation of the methanol and recrystallization of the products from toluene at −15° C. was then carried out. Further purification was carried out by sublimation under 0.2 mm Hg at a temperature just below melting point. The product was F(CF$_2$)$_8$(CH$_2$)$_6$OH. Analysis on the product gave the following result: $^1$H NMR (CDCl$_3$, δ in ppm), 1.35 (t, 1H, CH$_2$OH), 1.40 (4H, (CH$_2$)$_2$CH$_2$CH$_2$OH), 1.60 1.57 (4H, CF$_2$CH$_2$CH$_2$, and CH$_2$CH$_2$OH), 2.07 (2H, CF$_2$CH$_2$), 3.64(2H,CH$_2$OH). The F(CF$_2$)$_8$(CH$_2$)$_6$OH was converted to F(CF$_2$)$_8$(CH$_2$)$_6$Br as follows: In a 100 ml round-bottom flask 4.0 g (10 mmol) F(CF$_2$)$_8$(CH$_2$)$_6$OH and 4.97 g (0.015 mol) carbon tetrabromide was dissolved in tetrahydrofuran/CH$_2$Cl$_2$ (10 ml/20 ml) solution and cooled down to −5° C. using a brine bath. Then 3.93 g (15 mmol) triphenylphosphine was added in small portions over 15 minutes. The reactant was maintained at −5° C. for one hour and then at room temperature for 6 hours. As reaction proceeded, triphenylphosphine oxide was produced and the solvent became slightly pink due to formation of free bromine. The solvent was rotoevaporated and the products were extracted in 10 ml diethyl ether four times. The crude semifluorinated 1-bromoalkane was purified by reduced pressure distillation. Further purifying was then carried out by passing the partly purified product through a short silica column (12 cm) to absorb the triphenylphosphine oxide followed by subliming in a 0.2 mm Hg vacuum at a temperature just below the melting point. Analysis of the $F(CF_2)_8(CH_2)_6Br$ product gave $^1H$ NMR (CDCl$_3$, δ in ppm), 3.41 (t, 2H, CH$_2$Br) 2.06 (2H,CF$_2$CH$_2$), 1.84 (2H, CH$_2$CH$_2$Br), 1.60 (2H, CF$_2$CH$_2$CH$_2$), 1.45 (4H, CF$_2$CH$_2$CH$_2$CH$_2$CH$_2$); mp=35–37° C.

The polyamide was reacted with the semifluorinated 1-bromoalkane as follows: In a 25 ml flask, 0.34 g (3 mmol) polyamine was dissolved in a solution of 2 ml absolute ethanol and 1 ml N,N'-dimethylformamide and then 2.03 g (3.5 mmol) of semifluorinated 1-bromoalkane was added. Then the air was exchanged with nitrogen and the reaction was maintained at 70° C. for three plus weeks. The polymer was worked up by slow precipitation in diethyl ether and washing with warm diethyl ether several times to remove unreacted semifluorinated 1-bromoalkane. This was followed by drying in a vacuum oven overnight. The product was obtained in an amount of 1.80 g (86% yield). X-ray diffraction patterns on the product obtained by using a SCINTAG Θ—Θ diffractometer with Ni-filtered Cu X-ray tube (Kα=1.5418 angstroms, operated at 45 KV and 40 mA with continuous scans being performed at rates os 0.5 degrees–1 degree/minute gave d spacing in angstroms for film form of 45.5, 23.2, 15.5 and 11.41 and for powder form of 42.2, 28.5, 21.3, 14.3 and 5.08. Powered samples for X-ray diffraction are obtained from either solution precipitation or non-equilibrium processing. The weight average molecular weight of the fluorinated polymer is 2×10$^4$.

EXAMPLE XI

Synthesis of Fluorinated Polymer of the Formula (III) Where t is 0.85, x is 0.15, q is 8 and s is 10 and the Ratio q to r is 0.8 to 1

The synthesis was carried out the same as in Example X with equimolar amounts of reactants being used except that the semifluorinated 1-bromoalkane was $F(CF_2)_8(CH_2)_{10}Br$.

The $^1H$ NMR results for the $F(CF_2)_8(CH_2)_{10}OH$ intermediate were $^1H$ NMR (CDCl$_3$ δ in ppm), 1.36(1H, CH$_2$OH), 1.39 (12H, (CH$_2$)6 CH$_2$CH$_2$OH), 1.56 (4H, CF$_2$CH$_2$CH$_2$, and CH$_2$CH$_2$OH), 2.07 (2H, CF$_2$CH$_2$), 3.64 (2H, CH$_2$OH).

The analytical results for the $F(CF_2)_8(CH_2)_{10}Br$ intermediate were $^1H$ NMR (CDCl$_3$ δ in ppm), 3.40 (t, 2H, CH$_2$Br), 2.06 (2H, CF$_2$CH$_2$), 1.84 (2H, CH$_2$CH$_2$Br), 1.60 (2H, CF$_2$CH$_2$CH$_2$), 1.30 (12H, CF$_2$CH$_2$CH$_2$(CH$_2$)6CH$_2$CH$_2$Br); mp=41–43° C.

The fluorinated polymer product was obtained in an amount of 1.9 og (85% yield). X-ray diffraction patterns obtained as in Example X gave d spacing in angstroms for film form of 56.0, 27.9, 18.8 and 14.2 and for power form of 55.3, 33.1, 27.5, 16.6 and 5.06. The weight average molecular weight of the polymer is 2×10$^4$.

EXAMPLE XII

Synthesis of Fluorinated Polymer of the Formula (III) Where t is 0.85, x is 0.15, q is 10 and s is 10 and the Ratio q to r is 1 to 1

The synthesis was carried out as in Example X with equimolar amounts of reactants being used with the following exceptions.

The semifluorinated 1-bromoalkane was $F(CF_2)_{10}(CH_2)_{10}Br$.

The $F(CF_2)_{10}(CH_2)_{10}OH$ intermediate was prepared in a reaction where the reaction mixture was heated to 90° C. instead of to 80° C. The $^1H$ NMR results were the same as for $F(CF_2)_8(CH_2)_{10}OH$ (see Example XI).

In the conversion of $F(CF_2)_{10}(CH_2)_{10}OH$ to $F(CF_2)_{10}(CH_2)_{10}Br$, cooling was to 5 to 10° C. instead of to –5° C. and the reaction was maintained at 5–10° C. for the first hour instead of at –5° C.

The $^1H$ NMR results for $F(CF_2)_{10}(CH_2)_{10}Br$ were the same as for $F(CF_2)_8(CH_2)_{10}OH$ (see Example XI). The melting point result for $F(CF_2)_{10}(CH_2)_{10}Br$ was 64–66° C.

The fluorinated polymer product was obtained in an amount of 2.19 g (83% yield).

The weight average molecular weight of the fluorinated polymer is 3×10$^4$.

EXAMPLE XIII

Synthesis of Fluorinated Polymer of the Formula (III) Where t is 0.85, x is 0.15, q is 12 and s is 10 and the Ratio q to r is 1.2 to 1

The synthesis was carried out as in Example X with equimolar amounts of reactants being used with the following exceptions.

The semifluorinated 1-bromoalkane was $F(CF_2)_{12}(CH_2)_{10}Br$.

The $F(CF_2)_{12}(CH_2)_{10}OH$ intermediate was prepared in a reaction where the reaction mixture was heated to 100° C. instead of to 80° C. The $^1H$ NMR results were the same as for $F(CF_2)_8(CH_2)_{10}OH$ (see Example XI).

In the conversion of $F(CF_2)_{12}(CH_2)_{10}OH$ to $F(CF_2)_{12}(CH_2)_{10}Br$, cooling was to 5 to 10° C. instead of to –5° C. and the reaction was maintained at 5–10° C. for the first hour instead of at –5° C.

The $^1H$ NMR results for $F(CF_2)_{12}(CH_2)_{10}Br$ were the same as for $F(CF_2)_8(CH_2)_{10}Br$ (see Example XI). The melting point result for $F(CF_2)_{12}(CH_2)_{10}Br$ was 93–95° C.

The fluorinated polymer product was obtained in an amount of 1.48 g (79%).

X-ray diffraction patterns obtained as in Example X gave d spacing in angstroms for film form of 67.0, 33.4, 22.5 and 16.9 and for power form of 65.6, 32.5, 21.6 and 4.91. The weight average molecular weight of the fluorinated polymer is 3×10$^4$.

COMPARATIVE EXAMPLE II

Fluorinated Polymer of Formula (III) Where t is 0.83, x is 0.17, q is 8 and s is 4 and the Ratio q to r is 2.0 to 1

The synthesis was carried out as in Example X with equimolar amounts of reactants being used except that the semifluorinated 1-bromoalkane was $F(CF_2)_8(CH_2)_4Br$ and the alcohol intermediate for making the semifluorinated 1-bromoalkane was $F(CF_2)_8(CH_2)_4OH$.

The advancing water contact angle in a dry film was determined to be 121 degrees and the receding water contact angle in a dry film was determined to be 111 degrees.

FIG. 2 depicts data in respect to this fluorinated polymer according to time immersed in water. As shown in FIG. 2, contact angle was reduced substantially after 20 minutes immersion in water showing that this polymer does not provide stable low surface energy properties and is characterized by surface reconstruction after immersion in water.

Many variations of the above will be obvious to those skilled in the art. Thus, the invention is defined by the claims.

What is claimed is:

1. Fluorinated polymer for providing a low surface energy surface which is stable on immersion in water, said fluorinated polymer having a weight average molecular weight ranging from about $1 \times 10^3$ to about $1 \times 10^6$ and not containing moiety bearing a charge and comprising backbone containing (a) methylene groups and (b) side chain bearing groups

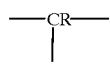

where C is a backbone atom and R is selected from the group consisting of hydrogen and alkyl containing 1 to 6 carbon atoms, and side chain on each side chain bearing group, said side chain having the formula —R'—O—C(O)—(CH$_2$)$_{p-1}$—(CF$_2$)$_q$F where R' is alkylene or isoalkylene containing 1 to 10 carbon atoms and the fluoroalkyl group of said side chain is spaced by r atoms from atom of the backbone to which R' is attached, wherein q ranges from 6 to 15, r ranges from 6 to 18, p is r minus 1 minus the number of chain atoms in R', and the ratio of q to r ranges from 0.6:1 to 1.8:1.

2. The fluorinated polymers of claim 1 having the formula

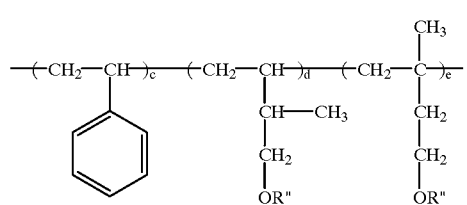

(I)

wherein c ranges from 0 to 0.99, d ranges from 0.6 to 0.006 and e ranges from 0.4 to 0.004 where c+d+e equals 1.0, and

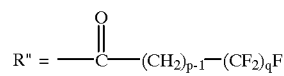

3. The fluorinated polymers of claim 2 wherein c is 0.786, d is 0.127 and e is 0.085.

4. The fluorinated polymer of claim 3 wherein q is 8 and p is 4.

5. The fluorinated polymer of claim 3 wherein q is 8 and p is 6.

6. The fluorinated polymer of claim 3 wherein q is 8 and p is 10.

7. The fluorinated polymer of claim 3 wherein q is 10 and p is 10.

8. The fluorinated polymers of claim 1 having the formula

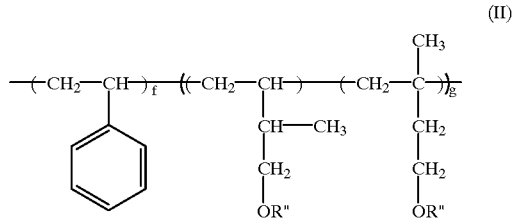

(II)

wherein f ranges from 0 to 0.99 and g ranges from 1.0 to 0.01 where f+g equals 1.0, and

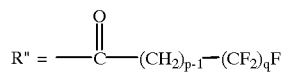

9. The fluorinated polymer of claim 8 wherein f is 0, g is 1.0, p is 4 and q is 8.

10. The fluorinated polymer of claim 8 wherein f is 0.23, g is 0.77, p is 4 and q is 8.

11. The fluorinated polymer of claim 8 wherein f is 0.42, g is 0.58, p is 4 and q is 8.

12. The fluorinated polymer of claim 8 wherein f is 0.81, g is 0.19, p is 4 and q is 8.

13. The fluorinated polymer of claim 8 wherein f is 0.93, g is 0.07, p is 4 and q is 8.

* * * * *